(12) United States Patent
Bader et al.

(10) Patent No.: US 7,016,788 B2
(45) Date of Patent: Mar. 21, 2006

(54) METHODS FOR CLASSIFYING NUCLEIC ACIDS AND POLYPEPTIDES

(75) Inventors: Joel S. Bader, Stamford, CT (US); Yi Liu, San Diego, CA (US); Darius M. Dziuda, North Haven, CT (US)

(73) Assignee: CuraGen Corporation, Branford, CT (US)

( * ) Notice: Subject to any disclaimer, the term of this patent is extended or adjusted under 35 U.S.C. 154(b) by 465 days.

(21) Appl. No.: 09/900,621

(22) Filed: Jul. 6, 2001

(65) Prior Publication Data

US 2002/0146706 A1 Oct. 10, 2002

Related U.S. Application Data

(60) Provisional application No. 60/216,610, filed on Jul. 7, 2000.

(51) Int. Cl.
*G01N 33/48* (2006.01)
*G06F 19/00* (2006.01)
(52) U.S. Cl. .......................................... 702/19; 702/20
(58) Field of Classification Search ................ 435/6, 435/69.1; 702/19, 20
See application file for complete search history.

(56) References Cited

U.S. PATENT DOCUMENTS

| | | | |
|---|---|---|---|
| 5,385,835 A | * | 1/1995 | Helentjaris et al. ......... 800/267 |
| 5,604,100 A | | 2/1997 | Perlin |
| 5,683,880 A | | 11/1997 | Kamb |
| 5,871,697 A | | 2/1999 | Rothberg et al. ........... 422/68.1 |
| 5,972,693 A | | 10/1999 | Rothberg et al. |

FOREIGN PATENT DOCUMENTS

| | | |
|---|---|---|
| WO | WO 99/07896 | 2/1999 |
| WO | WO 99/28505 | 6/1999 |
| WO | WO 00/15851 | 3/2000 |

OTHER PUBLICATIONS

Shimkets, et al. (1999). "Gene expression analysis by transcript profiling coupled to a gene database query." *Nat. Biotechnol.* 17(8): 798-803.

* cited by examiner

*Primary Examiner*—Ardin H. Marschel
(74) *Attorney, Agent, or Firm*—Mei L. Benni

(57) ABSTRACT

The present invention provides novel methods to identify, classify, quantify and compare nucleic acids and polypeptides.

36 Claims, No Drawings

METHODS FOR CLASSIFYING NUCLEIC ACIDS AND POLYPEPTIDES

RELATED APPLICATION

This application claims priority to U.S. Ser. No. 60/216,610, filed Jul. 7, 2000, which is incorporated herein by reference in its entirety.

FIELD OF THE INVENTION

This invention generally relates to nucleic acid sequence classification, identification, determination, and quantitation; more particularly it is the quantitative classification, comparison of expression or identification of preferably all nucleic acid sequences in one or more populations of nucleic acids.

BACKGROUND OF THE INVENTION

The ability to understand and treat complex disorders like cancer, heart disease, and diabetes is limited by our knowledge of the manifold genetic and environmental factors that contribute to disease initiation and progression. This need has driven the development of genomics technologies that merge brute-force data generation with sophisticated computational analysis to provide a comprehensive picture of biological processes. Early work in genomics focused on genome sequencing technologies, which aim to provide a catalog of the genetic blueprint of an organism. This static catalog, however, does not provide direct information about the dynamic interplay between gene expression levels and environmental factors relevant to disease.

Gene expression analysis is a type of genomics technology that provides a snapshot of the expression levels of the various genes within a biological sample such as a cell line, a tissue, an organ, or a whole organism. The RNA transcripts are extracted from cells, and the abundances of different species are measured. By measuring gene expression levels at different experimental conditions, for example at disease progression time points, at different developmental stages, for different disease models, or for different therapeutic treatments, genes can be associated with medically and scientifically relevant biological processes.

One method for gene expression profiling, known as expressed sequence tag (EST) sequencing, is to generate a cDNA library from a biological sample, then sequence a number of clones from the library. Sequencing typically starts from the 3' end of a transcript, generating a unique and reproducible sequence tag for each transcript. The number of times each tag is sequenced is tabulated, yielding a measurement of transcript abundance. The limitation of this method is that it is not able to provide reliable expression level measurements for genes expressed at low abundance. If 1000 tags are sequenced, for example, only genes expressed at a level of 1:1000 or greater will be typically detected. In a tissue of typical complexity, 10,000 or more transcripts are present, and a typical abundance is 1:10,000, below the sensitivity threshold of EST sequencing.

Serial analysis of gene expression (SAGE) is an improved method of EST sequencing in which terminal regions of multiple transcripts are concatenated prior to sequencing, providing approximately a 10-fold improvement in sensitivity. Even with this improvement, however, SAGE is costly and time-consuming.

More recent methods of gene expression analysis employ hybridization of nucleic acid sequences generated from transcript pools to microarray or chip surfaces to which have been attached complementary nucleic acid sequences. These methods are restricted to probing the expression levels of known genes. Preparing the nucleic-acid-derivatized surfaces can be a costly and time-consuming limitation. Background hybridization limits the sensitivity of these methods to low-abundance genes. Cross-hybridization between homologous genes with high sequence identity, for example 70% or greater, limits the selectivity of hybridization methods. Cross-hybridization can also limit the ability to distinguish between splice variants and allelic variants, including single nucleotide polymorphism (SNP) variants that are gaining importance as markers for association studies.

Differential display methods provide an alternative approach for measuring gene expression levels. These methods start with an RNA transcript pool, possibly in the form of cDNA, then use restriction enzyme (RE) pairs or primer pairs to selectively amplify fragments from certain transcripts within the pool. The fragments are analyzed experimentally, typically using gel electrophoresis, to generate a characteristic banding pattern in which the position of a band corresponds to the length of a fragment and the intensity of the band corresponds to the abundance of the fragment. Comparing banding patterns generated by different samples permits the identification of bands whose intensities vary, corresponding to differentially expressed genes. By performing this process using different RE pairs or primer pairs, the majority of transcripts in the original pool generate fragments that can be detected. This method can detect fragments from genes expressed at low levels, 1:50,000 or less, on par with or better than the levels achievable by competing technologies such as hybridization. Differential display also provides the capability to distinguish between homologs and variants by precise determination of size polymorphisms and by the presence or absence of restriction sites even in closely related sequences. A key advantage of differential display over hybridization approaches is that knowledge of transcript sequences is not a prerequisite to experimental analysis.

In its original form, differential display had a significant drawback in the lack of a convenient method to identify the particular nucleic acid sequence, including a gene, responsible for a band in a differential display pattern. In order to determine the gene sequence responsible for a differentially expressed band, it was necessary to physically isolate the DNA sequences generating the band, requiring cutting out a piece of electrophoresis gel, eluting the DNA, and sequencing several clones. After identifying one or more distinct DNA sequences, then one proceeded to use other techniques to conclusively identify the particular sequence that was differentially expressed.

Rothberg et al. describe a method for alleviating the difficulty of this procedure by comparing experimentally detected bands to a database of bands predicted for known gene sequences (U.S. Pat. No. 5,871,697; Shimkets et al. 1999 Nature Biotechnology 17:798–803). Furthermore, a method for rapidly confirming a band prediction made by differential expression and database lookup involves conducting an amplification procedure for detecting the band in the presence of an inhibitory primer that typically is nonlabeled. Thus, even if amplification occurs, the amplicon will not be detected. This procedure is termed "poisoning" herein; use of terms such as "poisoned" and so forth in the description also relates to this procedure. Poisoning is described in full in U.S. Ser. No. 09/381,779 filed Aug. 7, 1998, incorporated herein in its entirety.

In practice, there are two primary limitations of this method. The first limitation is that the height of a particular band provides a relative, rather than absolute, measure of gene expression. Comparing the height of a particular band between different samples provides an estimate of relative expression of the gene responsible for the band that is reliable for +/−1.5-fold ratios. Comparing heights of bands from different genes within a single sample does not, however, indicate the relative absolute abundance of these two genes. This limitation is common to many gene expression methods. Consequently, many profiles are expressed in terms of n-fold ratio compared to an arbitrary reference state.

The second limitation is providing a reliable band-to-gene database look-up. Often, a database look-up provides multiple sequences that could correspond to a particular band, whether differentially expressed or not. Even with the physical confirmation method described above, it is inefficient to use trial-and-error to test each sequence that could have contributed a band. Furthermore, even if only one particular nucleic acid sequence, including a gene, is predicted to generate a band corresponding to an experimentally detected band, it is still not definite that the gene actually did so. A gene sequence not in the database, for example, could be responsible.

Ranking the sequences in order of relative likelihood of generating the particular band would provide important aid to an experimentalist in interpreting a differential display pattern, or, more generally, of a direct read-out of peak heights following fragment generation from a cDNA pool. Another useful method would provide a numeric score, preferably in the form of either a probability or a p-value, that a particular nucleic acid sequence, including a gene, contributed a particular band.

SUMMARY OF THE INVENTION

The present invention provides methods for providing statistical scores for band-to-gene look-up from differential display experiments or fragment-based gene expression profiling. These methods are generally applicable for deconvolution of highly multiplexed signals.

In one embodiment, the statistical score is a probability that a particular nucleic acid sequence, including a gene, is expressed at a particular level, or level relative to a selected standard state, in a particular biological sample. The probability is preferably calibrated to match the probability that an independent experiment will confirm the predicted expression level.

In a second embodiment, the statistical score is a p-value that the experimental evidence for the expression level of a particular nucleic acid sequence, including a gene, is actually a false positive, and that the gene is not expressed at that level.

Either embodiment can serve to establish a cut-off low score such that genes with scores below the cut-off are assumed not to be expressed. The embodiments may be augmented to also provide a false-negative rate for nucleic acids or genes that are in fact expressed in a biological sample but whose scores do not rise above the cut-off value.

In the case of differential display experiments, the experimental signals are detected bands. The band-to-gene prediction is made by matching the detected bands to predicted bands. The predicted bands may arise from a purely computational prediction of expected fragment sizes or from a database of previously detected bands.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Experimental Data Generation
General Description

The present methods consider experiments designed to characterize the amounts, or relative amounts, of several species g in several experimental samples. The experiment operates on a particular species g to produce a signal B={b1, b2, . . . }, with the amount of signal proportional to the amount of species present. The experimental goal is to use the experimental signal B to perform two stages of prediction. The first stage is to predict which species g are present in each sample; the second stage is to predict the relative concentrations of species g across the samples.

These predictions are difficult because the signal B is subject to experimental uncertainty and because multiple species can produce overlapping signals. These result in false positive and false negative predictions for species presence or absence in the first stage, and in variation in the predicted concentrations in the second stage.

Independent samples and experimental replicates are two techniques typically employed to reduce errors in prediction. Independent samples are multiple samples that all correspond to a single experimental state or treatment. The variation between independent samples provides a measure of the inherent variation within a population and can provide statistical confidence for detected differences between populations. Experimental replicates are non-independent repeated experiments for a single sample. Variation between experimental replicates indicates the uncertainty in the data introduced solely by the experimental technique.

Differential Display

An important class of experiments is differential display. In this type of experiment, the species g are the nucleic acid sequences or genes expressed in a biological sample. General descriptions of differential display may be found in U.S. Pat. No. 5,871,697, and in Shimkets et al. 1999 Nature Biotechnology 17:798–803.

In a typical experiment, the samples are cell lines, tissues, organs, or whole animals, taken either singly or in pools. The RNA present in a sample is extracted, and then the mRNA is used as a template for synthesis of cDNA. The amount of cDNA serves as a proxy for the amount of corresponding mRNA transcript. Aliquots of cDNA are subjected to digestion by RE pairs to yield fragments as reaction products, the fragments are labeled, and the labeled fragments are separated by electrophoresis. The electrophoresis data may be represented as a trace of intensity vs. electrophoretic length. Methods for producing such traces are described in U.S. Ser. No. 09/398,404 filed Sep. 16, 1999, incorporated herein in its entirety. It is preferable to use a scaling function to normalize traces to have consistent intensities; these methods are also described in U.S. Ser. No. 09/398,404 filed Sep. 16, 1999, for example. If replicates are used, the preferable summary statistic to represent the sample intensity is the average of the replicates, although another summary statistics, such as the median, may also be used. The average trace for a sample may also include a measure of the experimental noise.

The electrophoretic separation collects identical fragments into a band b that appears as peaks in a trace. Each band is identified by the RE pair that generated the band and by the electrophoretic length of the band. The mobility of a fragment depends on its composition and its precise sequence of nucleotides. Thus, the electrophoretic length of a fragment is a fractional number rather than an integer number of nucleotides. The electrophoretic length is typically within +/−1.5 nt of the integer number of nucleotides. The measurement of electrophoretic length is subject to experimental variation in the range of +/−0.1 nt to +/−0.3 nt. Fragments with different nucleotide sequences may give rise to overlapping bands that are not resolved by electrophoresis.

Bands are preferably selected for analysis according to one of three modes: difference mode, query mode, or combination mode. These modes are described in the section "Detected Bands".

Proteomics

A second important class of experiments is proteome analysis by some combination of proteolysis, mass spectroscopy, and physical separation by HPLC or a related technique.

Detected Bands

Difference Mode

In difference mode, traces from a number of distinct samples are compared to identify bands whose intensities show significant variation between samples. Methods for identifying such bands are described in U.S. Ser. No. 09/398,404 filed Sep. 16, 1999, and are summarized below.

When multiple independent samples are available for each experimental state, a typical algorithm is to perform an f-test. The f-statistic for the f-test has a numerator corresponding to the between-treatment variation in the band intensity (treatment intensities calculated as averages of sample intensities, where the average can be the arithmetic mean, mode, or median) and a denominator corresponding to the within-treatment variation in the band intensity. The degrees of freedom for the f-test are as follows:

total number of degrees of freedom=(number of samples)−1;

between-treatment degrees of freedom=(number of treatments)−1; and within-treatment degrees of freedom=(number of samples)−(number of treatments).

The p-value for the f-statistic may be computed from tables available in works describing statistical methods or from suitable algorithms available in works describing statistical methods. A cut-off for the p-value is specified, and only bands whose p-values are lower than the cut-off are retained. A cut-off of 0.05 to 0.01 is typical. When only the bands that vary between treatments are desired, a one-sided f-test is appropriate, and bands having within-treatment variation greater than between-treatment variation are discarded.

It is also preferable to establish cut-offs for the overall variation. One method is to retain only differences for which the ratio of the highest intensity to the lowest intensity is greater than a cut-off value. A second method is to retain only differences for which the difference in intensity between the highest intensity and lowest intensity is greater than a cut-off value. These cut-offs may be enforced before, or preferably after, the p-value cut-off, and multiple variation cut-offs may be employed. Also, the high and low intensities may correspond to intensities for single traces, individual samples, or treatments, and the summary statistic used to calculate a sample or treatment intensity may be the median or, preferably, the mean of the contributing samples or traces.

An important special case of difference mode is a pairwise comparison between two treatments. The one-sided f-test for a pairwise comparison corresponds to a two-tailed t-test for a difference in band intensities between the two treatments. A preferable overall variation cut-off for a pairwise comparison is an ratio of 2-fold or greater of the higher treatment intensity to the lower treatment intensity.

It is preferable to prevent any two different bands from occurring within a minimum distance d from each other, where d is preferably larger than range used for band matching. A preferable value for d is 1.0 to 1.1 nt.

A preferable algorithm for adding difference bands under this constraint is to proceed as follows for each RE pair in turn:

1. Calculate p-values for all the locations where at least one sample has a band.
2. Sort the bands from low p-value to high p-value.
3. Repeat the following steps until the list is empty:
   3a. Save the top band from the list as a difference band; and
   3b. Remove any bands of lower p-value and within a distance d of the saved band.

Query Mode

In query mode, intensities are measured for bands at pre-determined positions. These pre-determined positions typically correspond to electrophoretic lengths for the following types of DNA fragments:

1. Fragments whose DNA sequence is known in its entirety;
2. Fragments whose DNA sequence is known partially, usually at one or both ends; and
3. Fragments whose DNA sequence is not known, but which have been physically isolated and may be conveniently and rapidly sequenced.

Combination Mode

Combination mode yields the union of the bands from difference mode and the bands from query mode. This can be preferably achieved by measuring the bands for query mode, then searching for bands in difference mode where the search is restricted to regions at least a width d away from any previously added difference band, where d has the same meaning as in difference mode.

Finding Bands in Good Data

Due to electrophoretic variation, a particular band i might not occur at the same exact location in every sample s. Instead, the distance might vary by +/−0.1 to 0.3 nt. Also, a band might not occur in every sample. The gene might not be expressed in every sample, for example, or the gene might have allelic variants that cause the band to shift by one or more nucleotides or to disappear entirely.

Thus, when samples are compared in either difference mode or query mode, it is preferable to start with a known band location, for example the location of band detected in another sample or in a previous experiment, and then to search for a matching band in the sample of interest within a range comparable to the experimental variation in band length. Thus, if the experimental variation is +/−0.1 to 0.3 nt, an appropriate range for band matching is +/−0.3 to 0.9 nt. If multiple bands occur within the range in the sample of interest, the band closest to the known length is preferably selected. Alternatively, the most intense band within the range is selected. The intensity b(i,s) of band i in sample s is then set to the height of designated peak.

If no band is found in the sample of interest, or equivalently no peak is present, the intensity must be estimated. Possible choices for the intensity b(i,s) of band i in sample s are as follows:

1. Use a fixed nominal baseline intensity.
2. Read the intensity in the second sample at the exact location of the band in the first sample.
3. Read the maximum intensity in the second sample within the search range relative to the location of the band in the first sample.

Choices 1 and 2 are preferable, with choice 2 most preferable.

It is also preferable to define an indicator variable peak (i,s) with peak(i,s)=1 if a peak was detected for band i in sample s, and peak(i,s)=0 if no peak was detected.

Missing Data

Occasionally, data may be missing for a subset of samples and RE pairs. This can occur, for example, when different sets of RE pairs are used to analyze different samples, or when experimental failure results in loss of data. Failing to find a band because of missing data is preferably treated differently from failing to find a band when there is good data, which is described in the section "Missing Bands in Good Data".

An indicator variable data(i,s) is defined to indicate whether sample s has good data for band i, with data(i,s)=1 when sample s has good data for band i (even if peak(i,s)=0), and data(i,s)=0 when sample s is missing data for band i.

When data(i,s)=0, b(i,s) is assigned an arbitrary value, preferably 0, than will be seen to be irrelevant in subsequent operations.

Methods for treating missing data and methods for treating missing bands without missing data are described in the appropriate sections below.

Transformed Band Intensities

It is preferable to replace the intensity of band i in sample s, b(i,s), with a log-transform, new $b(i,s)=\ln[b(i,s)]/\ln[x]$, where ln is the natural logarithm and x is a convenient base for the logarithm, preferably 2. It is preferable to define a cut-off value b0 such that b0>0 and new $b(i,s)=\ln[b0]/\ln[x]$ when b(s)<b0.

For each band i, it is also permissible to shift b(i,s) by subtracting a fixed quantity, such as the median or mean of b(i,s) over all the samples or a particular subset of samples.

Alternatively, without a log transform, the intensities for each band i may be modified by dividing by an intensity corresponding to a median or mean of b(i,s) over all the samples or a particular subset of samples.

Paired Controls

It is sometimes preferable to compare expression in an experimental sample with expression in a paired control, or set of paired controls, before comparing across experimental samples. In this case, it is preferable to calculate the intensity b(i,s) for peak i in experimental sample s by dividing by the mean or median intensity of the band intensity in the matched control. Afterwards, a log-transform may be applied. Alternatively, the log-transform may be applied first and then the mean or median of the control values may be subtracted from the experimental values.

Predicted Bands

Each nucleic acid sequence or gene g is associated with zero or more predicted bands B'={b1', b2', . . . }. The criteria for g being present depend on the band detection mode. Detecting these predicted bands in an experiment provides evidence for the presence of nucleic acid sequence or gene g in a sample.

In difference mode, presence of nucleic acid sequence or gene g means that nucleic acid sequence or gene g has a significant variation in expression level across the samples. In query mode or combination mode, presence of nucleic acid sequence or gene g means that its relative expression level can be determined for each of the samples, regardless of its variation.

The band-to-gene algorithm requires matching detected bands with predicted bands. It is also necessary to estimate the statistical confidence of the matching in terms of a false-positive rate (g is not present but a predicted band is detected) and false-negative rate (g is present but a predicted band is not detected) for each predicted band.

Search Window

A preferable algorithm for matching detected bands with predicted bands is as follows.

Each predicted band has a search window w such that it matches a detected band if there is at least one detected band within distance +/−w of the predicted band. The value w is preferably comparable to the precision of the estimate of the electrophoretic length of the predicted band.

If the electrophoretic length of the predicted band has not been measured experimentally, for example the band was predicted by a computational search for internal fragments flanked by sequences recognized by an RE pair, then the search window is preferably the expected precision of a computational prediction of the fragment electrophoretic length from its nucleotide sequence. A preferable prediction of the electrophoretic length is based simply the number of nucleotides of a fragment, and a preferable choice for w is 1.5 nt.

If the electrophoretic length of the predicted band has been determined, the search window is preferably the experimental precision of electrophoretic length, or w=0.1–0.3 nt. The electrophoretic length might be known from a previous experiment in which a band at a certain location was ascertained, to some degree of statistical certainty, to correspond to a specific nucleic acid sequence or gene sequence. The statistical certainty preferably does not affect the size of the search window, but it can modify the false-positive and false-negative rates as described below.

False-Positive Rate

For a particular nucleic acid sequence, including a nucleic acid sequence or gene, g and predicted band b with good data, the false-positive rate P(b|−g) is the conditional probability that the band is detected given that the nucleic acid sequence or gene is not present. The false-positive rate depends on the size of the search window such that if a first search window is entirely included in a second search window then the first P(b|−g) is less than or equal to the second P(b|−g). Each band-nucleic acid sequence or gene combination may have its own false-positive rate P(b|−g).

The false-positive rate is preferably estimated by fitting the final band-to-nucleic acid sequence or gene probability to experimental results by measuring the probability that a detected band known to correspond to a first nucleic acid sequence or gene is within the search window for a predicted band for a second nucleic acid sequence or gene. The false-positive rate $P(b|-g)$ may be calculated in this manner for predicted bands that have been detected and confirmed, then extrapolated to other predicted bands. For a simplified approach, it is preferable to use a single value alpha for the false-positive rate for all predicted bands with a given size search window.

It is also possible to estimate the false-positive rate. A preferable estimate for the probability may be obtained using the formula $$P(b|-g)=1-\exp[-2wf],$$

where the search window for band b extends +/−w from the predicted position and the frequency of detected bands is f.

The theoretical formula is useful because it provides a simple, rapid method for estimating the false-positive rate as a function of relevant factors, including the following:
  the detection mode (difference, query, or combination);
  the fragment length and RE pair, and the experimental band frequency as a function of fragment length and RE pair;
  the overall frequency of detected bands;
  the sequence information available for the detected band and predicted band;
  the expression level detection threshold;
  the type of biological sample used in the experiment, and previous evidence of expression of this nucleic acid sequence or gene in a related sample.

False-Positive Rate with Additional Sequence Information

In some instances, the appropriate false-positive rate is obtained indirectly. This occurs, for example, if a detected band b is matched to a predicted band b' of known length, and the assumption that b' was generated by nucleic acid sequence or gene g is itself subject to statistical uncertainty. This is especially useful when additional sequence information about band b' reduces the overall false-positive rate. A preferable formula for the false-positive rate is $$P(b'|-g)=1-[1-P(b|-b')][1-P(b|-g)],$$

where $P(b|-b')$ is the probability that the detected band is not the same as the known band, and $P(b'|-g)$ is the probability that the known band did not come from nucleic acid sequence or gene g.

False-Negative Rate

The false-negative rate $P(-b|g)$ is the conditional probability given that nucleic acid sequence or gene g is present and there is good data that no detected band is within the search window of predicted band b. This probability is preferably estimated experimentally by calculating the fraction of predicted bands that are detected for nucleic acid sequence or genes known to be present in a sample, then extrapolated to other nucleic acid sequence or genes. The false-negative rate may depend on factors including the following:
  the quality and stability of the mRNA or cDNA starting material;
  the reaction conditions used to generate fragments, including restriction enzymes and polymerases;
  the length and nucleotide sequence of the predicted fragments;
  the offset of the fragment from the 3' terminus of the mRNA transcript;
  the expression level detection threshold.

Each band-nucleic acid sequence or gene combination may have its own false-negative rate $P(-b|g)$. For a simplified approach, it is preferable to use a single estimate beta for all band-nucleic acid sequence or gene combinations having the same size search window.

Bayesian Gene Prediction
Consensus Modulation Band Filter

When a nucleic acid sequence or gene has multiple predicted bands that can be compared across independent samples, these bands should follow a consensus pattern of modulation across the individual samples. It is preferable to apply a consensus modulation band filter to modify the intensities of detected bands, which do not follow a consensus pattern of modulation.

A preferable algorithm for a multi-sample detected band filter is to proceed as follows.

1. For each nucleic acid sequence or gene, let $b(i,s)$ be the measured intensity of predicted band i in sample s, preferably after a log transform, and $data(i,s)$ be the good data indicator variable.

2. It is preferable to convert $b(i,s)$ to a z-score $z(i,s)$ that represents its normalized variation across samples as follows. Let
  $s0(i)$=sum over s of $data(i,s)$,
  $s1(i)$=sum over s of $data(i,s)\, b(i,s)$, and
  $s2(i)$=sum over s of $data(i,s)\, b(i,s)\, b(i,s)$.

Next, the average $avg(i)$ and sample standard deviation $stddev(i)$ of the intensity of band i are calculated as $$avg(i)=s1(i)/s0(i), \text{ and}$$

$$stddev(i)=\{[s2(i)-s1(i)s1(i)]/[s0(i)-1]\}^{\wedge}0.5.$$

In the special case that $s0(i)=1$ a fixed value, preferably 1, is used for $stddev(i)$. Finally, z-scores are calculated as $$z(i,s)=[b(i,s)-avg(i)]/stddev(i).$$

If z-scores are not used, then $z(i,s)$ is preferably defined as $b(i,s)$.

3. It is preferable to also calculate band-deleted sample averages $avg(i,s)$ and indicator variables $data1(i,s)$ as $$avg(i,s)=s1(i,s)/s0(i,s), \text{ where}$$

$s0(i,s)$=sum over j of $data(j,s)$ with $j<>i$;
$s1(i,s)$=sum over j of $data(j,s)\, z(j,s)$ with $j<>i$; and
$data1(i,s)=1$ if $s0(i,s)>0$ and 0 if $s0(i,s)=0$.

If $data1(i,s)=0$, then a preferable value for $s1(i,s)$ is 1.

Less preferably, $avg(i,s)$ for each band i may be set equal to a consensus value $avg(s)$, where $$avg(s)=s1(s)/s0(s), \text{ where}$$

$s0(s)$=sum over i of $data(i,s)$, and
$s1(s)$=sum over i of $data(i,s)\, z(i,s)$.

In this case, $ma(i,s)$ may be set to 1.

4. The correlation coefficient $corln(i)$ is calculated for each band i with the band-deleted sample average $avg(i,s)$. A preferable choice is the Pearson correlation coefficient, defined as $$corln(i) = [sum(i, a) - sum(i)sum(a)/n(i, a)] /$$
$$\{[sum(i, i) - sum(i)sum(i)/n(i, a)][sum(a, a) -$$
$$sum(a)sum(a)/n(i, a)]\}^{\wedge}0.5,$$

where
- sum(i,a)=sum over s of z(i,s) avg(i,s) data(i,s) data1(i,s);
- sum(i,i)=sum over s of z(i,s) z(i,s) data(i,s) data1(i,s);
- sum(a,a)=sum over s of avg(i,s) avg(i,s) data(i,s) data1(i,s);
- sum(i)=sum over s of z(i,s) data(i,s) data1(i,s);
- sum(a)=sum over s of avg(i,s) data(i,s) data1(i,s);
- n(i,a)=sum over s of data(i,s) data1(i,s).

5. The correlation corln(i) is compared to a cut-off value in order to determine whether band i actually corresponds to nucleic acid sequence or gene g. Possible criteria are as follows:
- corln(i)>=0, which indicates that the band is modulation is in the majority.
- corln(i)>c0, where c0 is independent of n(i,a).
- corln(i)>c0, where c0 depends on n(i,a) and is the threshold correlation for a p-value of p0 with n(i,a)−2 degrees of freedom. The threshold p0 is preferably 0.2.

An indicator variable det(i,g) is defined for band i and nucleic acid sequence or gene g such that
- det(i,g)=1 if the correlation is above the threshold, and
- det(i,g)=0 if the correlation is below the threshold.

If the consensus modulation filter is not employed, which is less preferable, then det(i,g)=1 always.

A band i is detected in sample s for nucleic acid sequence or gene g when peak(i,s) det(i,g)=1, and is not detected when peak(i,s) det(i,g)=0.

Expression Level

An expression level estimate E(g,s) for nucleic acid sequence or gene g in sample s based on detected bands may be obtained from a variety of methods as follows.
- E(g,s)=mean or median of b(i,s) where data(i,s)=1, counting all the good data for the nucleic acid sequence or gene and sample.
- E(g,s)=mean or median of b(i,s) where det(i,g) data(i,s)=1, counting all the consensus bands with good data for the nucleic acid sequence or gene and sample.
- E(g,s)=mean or median of b(i,s) where peak(i,s) data(i,s)=1, counting all the peaks for the nucleic acid sequence or gene and sample.
- E(g,s)=mean or median of b(i,s) where det(i,g) peak(i,s) data(i,s)=1, counting just the peaks which follow the consensus modulation.

Alternatively, if relative expression levels are desired, then z(i,s) defined for the consensus modulation filter may be used instead of b(i,s) in the formulas above.

Bayes Rule

The conditional probability P(g|B,−C) is defined as the probability that a nucleic acid sequence or gene is present in sample s when bands B={b(1), b(2), . . . , b(m)} are predicted and detected, while bands C={c(1), c(2), . . . , c(n)} are predicted but not detected. For simplicity, the sample identify s is assumed and does not appear in the notation.

The calculation of P(g|B,−C) starts with Bayes rule, $$P(g|B,-C)P(B,-C)=P(B,-C|g)P(g),$$

where P(B,−C) is the probability of detecting bands B but not bands C, P(B,−C|g) is the conditional probability of detecting bands B and not detected bands C when nucleic acid sequence or gene g is present, and P(g) is the prior probability that nucleic acid sequence or gene g is present. Similarly, $$P(-g|B,-C)P(B,-C)=P(B,-C|-g)P(-g)$$

where P(−g|B,−C) is the conditional probability of nucleic acid sequence or gene g not being present when bands B are detected and C are not, P(B,−C|−g) is the probability that bands B are detected and C are not when nucleic acid sequence or gene g is not present, and P(−g) is the prior probability that nucleic acid sequence or gene g is not present.

Using the identity $$P(g \text{ or } -g|B,-C)=P(g|B,-C)+P(-g|B,-C)=1,$$

which is true because g and −g are disjoint and 1 must always be true leads to the expression $$P(g|B,-C)=[P(B,-C|g)P(g)/P(B,-C)]/[P(B,-C)P(g)/P(B,-C)+P(B,-C|-g)P(-g)/P(B,-C)],$$

or, simplifying, $$P(g|B,-C)=1/\{1+[P(B,-C|-g)/P(B,-C|g)][P(-g)/P(g)]\}.$$

The quantities on the right hand side of this expression are calculated or estimated as follows.

$$P(B,-C|-g)=\text{product over } i \ \{p(b(i)|-g)\} \text{ product over } j \ \{1-p(c(j)|-g)\};$$

$$P(B,-C|g)=\text{product over } i \ \{1-p(-b(i)|g)\} \text{ product over } j \ \{p(-c(j)|g)\};$$

$$P(-g)/P(g)=\text{odds that a nucleic acid sequence or gene is not expressed.}$$

The fraction P(−g)/P(g) depends on the nucleic acid sequence or gene and the experiment. A preferable estimate for P(−g)/P(g) in difference mode is the number of bands detected as differences divided by the total number of bands. A typical range of values is 1% to 5%.

P-Values

The p-value, or false-positive rate, for a prediction that a nucleic acid sequence or gene is expressed based on experimental data that predicted bands B are detected but predicted bands C are not detected is the sum of the conditional probability for this observation and all better observations.

The p-value may be calculated as follows:

1. For each possible partitioning of the predicted bands into B' detected bands and C' non-detected bands, calculate P(g|B',−C') according to the Bayes rule formula.

2. For a particular observation of B detected bands and C non-detected bands, the p-value is
- p-value(g|B,−C)=sum of P(B',−C'|−g) for all partitionings of predicted bands into B' detected and C' non-detected with P(g|B',−C')>=P(g|B,−C)
- and 0<=p-value(g|B,−C)<=1.

Simplified Bayes Formula and P-Value

In the case that p(b(i)|−g) is the fixed value alpha and p(−c(j)|g) is the fixed value beta, and there are D detected bands out of T total bands, the Bayes formula simplifies to $$P(g|D \text{ of } T)=1/\{1+[P(-g)/P(g)][\text{alpha}/(1-\text{beta})]^D [(1-\text{alpha})/\text{beta}]^{(T-D)}\}$$

This formula is preferable when it is reasonable to use one false-positive rate and one false-negative rate for each band, for each when the search window d for each band is the same width.

It is also preferable to fit the values alpha, beta, and P(−g)/P(g) to experimental data. A preferred fitting method is to minimize the chi-square difference between P(g|D of T) values from the Bayes formula and from experiments. A more preferred method is to constrain the fit by using pre-assigned values for alpha and beta. Methods for assigning values to alpha and beta have been described previously.

For the simplified Bayes formula with D detected bands out of T total bands, the p-value is p-value(g|D of T)=sum over D'=D ... T of Comb(T, D') P(g|D',T)=sum over D'=D ... T of Comb (T,D')/{ 1+[P(−g)/P(g)][alpha/(1−beta)]^D'[(1−alpha)/beta]^(T−D')}, where Comb(T,D)=combination of T items D at a time=T!/D! (T−D)! and Comb(T,0)=1, and D'=D ... T is the sequence D, D+1, D+2, ..., T.

When alpha, beta, and P(−g)/P(g) have fixed values and the simplified Bayes formula is appropriate, it is convenient to pre-compute P(g|D of T) and p-value(g|D of T).

To use the simplified formula, it is preferable that each band have the same size search window. This occurs, for example, when all the predicted bands are computer predictions without precise electrophoretic lengths, or when all the predicted bands have precise electrophoretic lengths. When different bands have different sized search windows, a number of simplified approaches are still possible. For example, when all bands have computer-predicted sizes and some bands have precise electrophoretic lengths, the following simplified approaches are possible, one a separate calculation and the second a joint calculation. These calculations have the following parameters:

There are T' bands with precise electrophoretic predicted lengths and T" bands without precise electrophoretic lengths. There are T bands with low-precision computer-predicted lengths, including all of the T" bands and zero or more of the T' bands.

Using a smaller search window, D' of T' bands are detected with a corresponding false-positive rate alpha' and false-negative rate beta'.

Using a larger search window, D" of T" bands are detected with a corresponding false-positive rate alpha" and false-negative rate beta".

Furthermore, using a larger search window for all the bands, D of T bands are detected, again with false-positive rate alpha" and false-negative rate beta".

Separate Calculation

Calculate P(g|D of T) and p-value(g|D of T) using alpha" and beta" for a larger search window, then recalculate P(g|D' of T') and p-value(g|D' of T') using alpha' and beta' for a smaller search window. Retain the results based on one of the following criteria: (1) if D'>0, use the results for electrophoretic lengths; (2) use the results giving the higher P(g|D of T); (3) use the results giving the lower p-value(g|D of T).

Joint Calculation

Calculate the Bayes probability as

P(g|D' of T', D" of T")=1/{1+[P(−g)/P(g)][alpha'/(1−beta')]^D' [(1−alpha')/beta']^(T'−D')[alpha"/(1−beta")]^D"[(1−alpha")/beta"]^(T"−D")}.

Display

It is preferable to display nucleic acid sequence or genes in ranked order. Preferable methods for ranking nucleic acid sequence or genes are as follows:

From high P(g|B,−C) to low P(g|B,−C), down to a cut-off probability.

From low p-value(g|B,−C) to high P(g|B,−C), up to a cut-off probability.

When nucleic acid sequence or genes are predicted based on both computer-predicted band lengths and electrophoretic band lengths, it is preferable t split the nucleic acid sequence or genes into two sets, the first with at least one detected band with a predicted electrophoretic length and the second with no detected bands with a precise electrophoretic length, rank each list separately according either method above, and then concatenate the lists for display.

It is preferable that the display indicates some or all of the following information:

P(g|B,−C)
p-value(g|B,−C)
E(g,s)
The detected bands B
The non-detected bands C
Whether each band has a predicted electrophoretic length
Information about the nucleic acid sequence or gene

EXAMPLES

Experimental Data Generation

The general experimental procedures employed in preparing samples, analyzing them and displaying the results obtained thereby are fully described, for example, in U.S. Pat. No. 5,871,697 and in Shimkets et al., "Gene expression analysis by transcript profiling coupled to a gene database query" Nature Biotechnology 17:198–803 (1999). These include removal of tissues and preparation of total RNA, preparation of cDNA therefrom and processing the resulting samples through up to 140 subsequences of GeneCalling™ analysis.

Experimental data are to be generated for rat samples. Approximately 2 to 6 or more rats are used, encompassing 2, 3, or 4, or more distinct treatments (e.g., sex, strain, drug, dosage). The rats are sacrificed and their livers removed.

Three separate aliquots of cDNA are used for triplicate reactions with 80 distinct restriction enzyme (RE) pairs to generate fragments. The fragments are fluorescently labeled and separated using capillary electrophoresis according to the methods referenced above. A calibration curve based on DNA fragments of known length is then used to generate a trace of intensity versus electrophoretic length for fragments in the size range 50 nt to 450 nt for each of the 3 treatments, 3 samples, 3 replicates, and 80 RE pairs, yielding 2160 individual traces. Excluding experimental failures, the majority of the individual traces generate reliably good data.

Traces are scaled according to U.S. Ser. No. 09/398,404 filed Sep. 16, 1999, by finding peaks (local maxima monotonically decreasing over 0.4 nt on each side), performing an overall normalization by multiplying each trace by an overall factor to set the median peak height to 100, then performing a fine scaling by minimizing the square distance, excluding outliers with a 3-fold difference or greater, between each trace and an average of the sample averages.

Detected Bands

Band detection proceeds separately for difference mode and query mode.

For difference mode, peaks are compared using a window of +/−0.1 to 0.8 nt, preferably +/−0.3 nt, to match peaks between samples, an exclusion distance of at least d=+/−0.3 to 1.5 nt, preferably +/−1.0 nt, between peaks, and a maximum p-value from an f-test on sample averages within and between treatments of 0.001. In pairwise comparisons with the control, approximately 0.1 to 10% of the bands are differentially expressed in each of the experimental treatments.

For query mode, intensities are extracted at the locations of the known electrophoretic lengths of the predicted bands corresponding to distinct transcribed sequences. A window of +/−0.1 to 0.8 nt, preferably +/−0.3 nt, is used for finding bands.

In both difference mode and query mode, peak(i,s) is set to 1 if at least one trace corresponding to sample s had a peak for band i.

Predicted Bands

Sequence Databases

Two GenBank sequence databases, the first for *Rattus* sp. and the second for *Homo sapiens*, are used as the source of predicted bands. Information about the databases is to be provided in a table such as that shown below ("avg" represents "average").

| Database | Rat | Human |
|---|---|---|
| # of transcripts | — | — |
| avg transcript length | — | — |
| avg # of predicted bands per RE and transcript | — | — |
| total # of known bands | — | — |
| # of transcripts with at least 1 known band (poisoned or 3+ trapped) | — | — |

A fixed search window of w=+/−0.3 nt is used for bands with known electrophoretic lengths, and a larger fixed search window of w=+/−1.5 nt is used for bands without known electrophoretic lengths.

False-Positive Rate

The false-positive rate $P(b|\sim g)=\alpha$ for difference mode for the larger search window is calculated from previous experiments as the ratio of the total number of detected bands to the total number of predicted bands for rat nucleic acid sequence or genes that are presumed to be absent.

False positives arise through a variety of ways, including, for example, the presence of overlapping bands. One way to confirm a band and to eliminate a false positive result is to carry out amplification with poisoning, i.e., in the presence of a nonlabeled inhibitory primer (see U.S. Ser. No. 09/381,779 filed Aug. 7, 1998). The resulting false-positive rate is alpha, and may range from about 0.05 to about 0.5, and is likely to be about 0.3.

Alternatively, the false-positive rate may be calculated as the ratio of detected bands to predicted bands for nucleic acid sequence or genes from a sufficiently unrelated species, such as human.

The false-positive rate for query mode for the smaller search window is calculated as the fraction of bands with known electrophoretic lengths for which a band from a different nucleic acid sequence or gene, also with a known electrophoretic length, is within +/−0.3 nt. The resulting false-positive rate is alpha may range from about 0.05 to about 0.5, and is likely to be about 0.2.

These results compare favorably with theoretical estimates of the false positive rate, developed as follows. The probability p1 that a transcript of length L nucleotides generates at least one band between A and B in length is $$p1 = 2\ r1\ r2\ \text{integral}\_0^{(L-A)} dx1\ \text{integral}\_{(x1+A)}^{\text{Min}(x1+B,L)} dx2 (1-r1-r2)^{(x2-x1)},$$

where r1 and r2 are the cutting frequencies of the two restriction enzymes, x1 and x2 are the positions along the transcript where the cuts occur, the factor of 2 accounts for interchanging the order of the first and second cut, and the factor $(1-r1-r2)^{(x2-x1)}$ indicates that the fragment from x1 to x2 has no internal cuts. For experiments such as those considered here, each restriction enzyme has a 6-nt recognition site, and $r1=r2=r$ is approximately equal to $1/4^6=1/4096$. Furthermore, cDNA synthesis typically extends only 2000 nt, and therefore L~2000 nt. Consequently, the product $r\ L<1$ and can be used as the variable for a Taylor-series expansion for p1. The lowest-order term in the expansion provides an acceptable estimate for p1, $$p1=2\ r^2\ L\ (B-A),$$

which is approximately equal to 2×2000 nt×(450 nt−50 nt)/(4000 nt×4000 nt)=0.1, or each transcript has approximately a 10% probability of producing at least one fragment with any given RE pair. The probability of producing two fragments is smaller than $p1^2$ and can be neglected, and the number of bands per nucleic acid sequence or gene is approximately 0.1 for each RE pair.

The total number of bands expected in the region from 50 nt to 450 nt is equal to (number of nucleic acid sequence or genes expressed)×(bands per nucleic acid sequence or gene) =1000 per trace, assuming 10,000 expressed nucleic acid sequence or genes. This number is larger than the approximately 400 bands typically observed per trace, or 1 band/nt. There are a number of explanations for this difference. First, the assumptions that each restriction enzyme cuts with a frequency of 1/4096 and that each transcript is 2000 nt result in overestimates of predicted bands when compared with database statistics. Second, a fraction of nucleic acid sequence or genes are expressed below a level required to be detected in the experiment. Finally, not every predicted band is detected, even for nucleic acid sequence or genes that produce some detected bands, as described in "False-Negative Rate" below.

Typically 1% of bands are detected as differences, or 0.01 band/nt. The estimated false-positive rate with a +/−1.5 nt window is then $$\alpha=1-\exp(-0.03)=0.03$$

for difference mode.

In query mode, the estimated false-positive rate for a band density of 1 band/nt is $$\alpha=1-\exp(-0.6)=0.45$$

for a +/−0.3 nt window for bands with known electrophoretic lengths. This result is reasonably close to the experimental result of 0.2 reported above.

For larger windows of +/−1.5 nt when the electrophoretic lengths are not known, $$\alpha=1-\exp(-3)=0.95,$$

and false positives are very likely.

False-Positive Rate with Additional Sequence Information

The estimated 0.95 false-positive rate for query mode can be reduced if additional sequence information is available for bands with known electrophoretic lengths. This example describes additional information in the form of known or degenerate sequence information at specific nucleotide positions in a fragment, for example at known offsets upstream or downstream of a recognition site. Other types of information may include extra sequence information at an unspecified location within a fragment, sequence composition, or more precise computer predictions of fragment mobility, for example if mass spectrometry were to be used instead of electrophoresis to provide fragment lengths.

The net effect of additional sequence information is to reduce the effective band frequency f used in the calculation of the false-positive rate, which then decreases the false-positive rate itself. For example, if one additional nucleotide of sequence information is available for a detected band, then the effective band density is decreased 4-fold.

Continuing with this example of sequence information at known positions, degenerate nucleotides count as fractional nucleotides of sequence information in this approach. The formula converting the frequency Freq of a possibly degenerate nucleotide to an effective number of nucleotides N(eff) is $N(\text{eff}) = -ln(\text{Freq})/ln(4)$.

Exemplary results calculated for N(eff) are given in the Table following:

| Degeneracy | Frequency | N(eff) | Examples |
|---|---|---|---|
| 1-fold (no degeneracy) | 1/4 | 1 | A, C, G, T |
| 2-fold | 1/2 | 0.5 | R, Y |
| 3-fold | 3/4 | 0.207519 | B, D |
| 4-fold (any) | 1 | 0 | N |

The total number of additional nucleotides, N(tot), is the sum of N(eff) at each position with additional information. For example, let the positions in a fragment next to recognition site for RE1 be denoted as R1 and R2, and the positions in the fragment next to the recognition site for RE2 as J1 and J2. The following table shows the amount of additional nucleotide information for a few examples.

| R1 | R2 | J2 | J2 | N(tot) |
|---|---|---|---|---|
| N | A | N | N | 1 |
| R | N | N | Y | 1 |
| C | G | N | B | 2.207519 |
| A | N | T | C | 3 |
| T | A | G | G | 4 |

The band density f for calculating false-positives is reduced by a factor 4^N(tot). The graph in the following figure shows the effective band density f(eff) and the final false-positive rate alpha(f) assuming an initial band densities of 3 bands/nt (thick line), 1 band/nt (medium line), and 0.333 bands/nt (thin line), and a +/−1.5 nt search window.

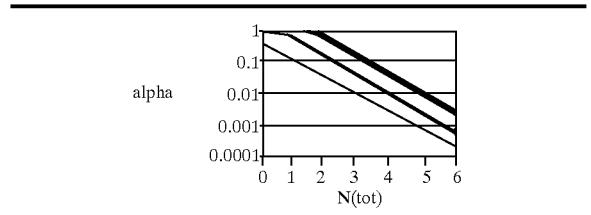

It may be recalled from the preceding discussion that the false-positive rate alpha for a band density of 1 band/nt and a search window of +/−1.5 nt is 0.95. When 3 extra nucleotides of sequence information are available, alpha drops to 0.046, even smaller than the false-positive rate for bands with known electrophoretic length.

A preferred method is to gather extra sequence information for the bands in a single control sample, then to use the known electrophoretic lengths of the bands to compare with bands in multiple experimental samples. When N(tot)>=3 nt, the final false positive rate is approximately alpha=1−(1−0.2)(1−0.046)=0.24, which is close to the false-positive rate for bands with known electrophoretic lengths in query mode.

In order to use the simplified Bayes formulas, bands with known electrophoretic length or with N(tot)>=3 nt are grouped together in a single set having the same overall alpha and beta values.

False-Negative Rate

The false-negative rate P(−b|g)=beta for computer-predicted bands in difference mode is calculated from experimental data as follows. First, the set of transcripts is identified as differentially expressed in previous experiments using rat samples based on confirmation of expression differences through poisoning. These transcripts are predicted to produce bands, of which a certain fraction are detected with windows of +/−1.5 nt. The final false-negative rate beta is the ratio of detected to predicted bands.

The false-negative for bands with known electrophoretic length in difference mode is calculated from the same set of experiments. The same number of differentially expressed transcripts are predicted to produce certain bands of known electrophoretic length, of which some are detected with windows of +/−0.3 nt. The final false-negative rate beta may be calculated from this information.

The false-negative rate for query mode should be lower than the false-negative rate for difference mode because a band might be present but not scored as a difference. The false-negative rate for query mode is not, however, calculated from experimental data, but rather estimated by a fit to the data (see below).

Bayesian Gene Prediction

Expression profiles for 2–5 individual drug-treated rats are compared with profiles for a similar number of individual controls matched for all parameters except drug treatment. Bands are detected in difference mode, with a 0.05 p-value threshold and a 1.5-fold variation threshold. For each pairwise comparison, a nucleic acid sequence or gene is judged to be present ("Pass") if at least one detected band is confirmed through the poisoning method and is judged to be absent ("Fail") if at least one detected band is not confirmed after a poisoning attempt and no detected band is confirmed.

Results are binned separately for the nucleic acid sequence or genes present and absent according to the number of detected bands and the number of predicted bands, both for computer-predicted lengths using a +/−1.5 nt window and for electrophoretic lengths using a +/−0.3 nt window. The experimental nucleic acid sequence or gene probabilities are displayed in the tables below. The pass likelihood is defined as (#pass)/(#pass+#fail) for each number of detected and predicted bands.

Next, the simplified Bayes formula is used to estimate the pass likelihoods. For a first set of parameters, the values for alpha and beta are set to values such as those obtained above, or similar values, and the ratio P(−g)/P(g) is set to a value that is a commonly arising ratio. A summary of the fit is provided in a table such as that shown below.

|  | Computer-Predicted Lengths | Electrophoretic Lengths |
|---|---|---|
| alpha | 0.3 | 0.2 |
| beta | 0.6 | 0.5 |

-continued

| | Computer-Predicted Lengths | Electrophoretic Lengths |
|---|---|---|
| P(−g)/P(g) | 0.02 | 0.02 |
| Chi-Square | — | — |
| p-value | — | — |

The p-value for the chi-square test is the probability the observed results, or any other results further from the Bayes results, when the Bayes results describe the expected results. A p-value of 0.05 or smaller typically indicates that a proposed distribution should be rejected.

Parameter sets are also selected to optimize a chi-square test between the observed likelihoods and the Bayes formula likelihoods for combinations of detected and predicted bands with 5 or more total trials, i.e., #pass+#fail>=5. The results are shown in a table such as that shown below.

| | Computer-Predicted Lengths | Electrophoretic Lengths |
|---|---|---|
| alpha | — | — |
| beta | — | — |
| P(−g)/P(g) | — | — |
| Chi-Square | — | — |
| p-value | — | — |

Results calculated according to the procedures and examples presented herein indicate that the Bayes formula result provides a convenient estimate of the likelihood, based on predicted and detected bands, that a particular nucleic acid sequence, including a gene, is present in a sample. To test the parameter sets, several pairwise comparisons are selected and all the nucleic acid sequence or genes with p-values above a given cut-off value are tested for presence or absence.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for comparing nucleic acids, said method comprising:
   (a) providing a first sample comprising a first population of first nucleic acids having different nucleotide sequences, and a second sample comprising a second population of second nucleic acids having different nucleotide sequences, wherein the nucleotide sequences of said second population are known;
   (b) probing said first sample with one or more recognition means, each recognition means recognizing a target nucleotide subsequence or a set of target nucleotide subsequences, wherein if said first sample is probed with two or more recognition means, each recognition means recognizes a different target nucleotide subsequence or a different set of target nucleotide subsequences;
   (c) generating one or more output signals from said first sample probed by said recognition means, each output signal comprising a representation of (i) the distance between occurrences of target nucleotide subsequences in said first nucleic acid, and (ii) the identities of said target nucleotide subsequences in said first nucleic acid or the identities of said sets of target nucleotide subsequences among which are included the target nucleotide subsequences in said first nucleic acid; and
   (d) comparing each representation provided by said first sample with said second population by generating (i) statistical score which states the probability that one or more output signals from said first sample indicates that one or more nucleotide sequences of said first sample are either present or absent in said second sample; and (ii) a statistical score of a false-negative rate or a false-positive rate, wherein said false-negative rate is a representation of the probability that said output from said first nucleic acid or said second nucleic acid is not generated given that said first or second nucleic acid is present, and said false-positive rate being a representation of the probability that said output from said first nucleic acid or said second nucleic acid is generated given that said first or second nucleic acid is not present.

2. The method of claim 1, wherein the output signals from said first sample indicate that one or more nucleotide sequences of said first sample are present in said second sample.

3. The method of claim 1, wherein the output signals from said first sample indicate that one or more nucleotide sequences of said first sample are absent in said second sample.

4. The method of claim 1, wherein said statistical score is generated according to Bayes Rule of conditional probability.

5. The method of claim 1, wherein said distance between occurrences of target nucleotide subsequences is pre-determined.

6. The method of claim 1, wherein said comparison is performed by generating (i) a statistical score which states the probability that one or more output signals from said first sample indicates that one or more nucleotide sequences of said first sample are either present or absent in said second sample; and (ii) a statistical score of a false-negative rate.

7. The method of claim 1, wherein said comparison is performed by generating (i) a statistical score which states the probability that one or more output signals from said first sample indicates that one or more nucleotide sequences of said first sample are either present or absent in said second sample; and (ii) a statistical score of a false-positive rate.

8. A method for comparing one or more nucleic acids, said method comprising:
   (a) providing a first sample comprising a first population of first nucleic acids having different nucleotide sequences, and a second sample comprising a second population of second nucleic acids having different nucleotide sequences, wherein the nucleotide sequences of said second population are not known;
   (b) probing said first sample with one or more recognition means, each recognition means recognizing a target nucleotide subsequence or a set of target nucleotide subsequences, wherein if said first sample is probed with two or more recognition means, each recognition means recognizes a different target nucleotide subsequence or a different set of target nucleotide subsequences;
   (c) generating one or more output signals from said first sample probed by said recognition means, each output signal comprising a representation of (i) the distance between occurrences of target nucleotide subsequences in said first nucleic acid, (ii) the identities of said target nucleotide subsequences in said first nucleic acid or the identities of said sets of target nucleotide subsequences among which are included the target nucleotide subsequences in said first nucleic acid; and (iii) a measure of the level/amount of the first nucleic acid in the first sample producing the output signal;

(d) performing steps (b) and (c) for said second sample; and (e) comparing the representation provided by said first sample with the representation provided by the second sample by generating (i) a statistical score which states the probability that one or more output signals from said first sample indicates that one or more nucleotide sequences of said first sample are either present or absent in said second sample; and (ii) a statistical score of a false-negative rate or a false-positive rate, wherein said false-negative rate is a representation of the probability that said output from said first nucleic acid or said second nucleic acid is not generated given that said first or second nucleic acid is present, and said false-positive rate being a representation of the probability that said output from said first nucleic acid or said second nucleic acid is generated given that said first or second nucleic acid is not present.

9. The method of claim 8, wherein the output signals from said first sample indicate that one or more nucleotide sequences of said first sample are present in said second sample.

10. The method of claim 8, wherein the output signals from said first sample indicate that one or more nucleotide sequences of said first sample are absent in said second sample.

11. The method of claim 8, wherein said statistical score is generated according to Bayes Rule of conditional probability.

12. A method for comparing one or more nucleic acids, said method comprising:

(a) providing a first sample comprising a first population of first nucleic acids having different nucleotide sequences, and a second sample comprising a second population of second nucleic acids having different nucleotide sequences, wherein the nucleotide sequences of said second population are not known;

(b) probing said first sample with one or more recognition means, each recognition means recognizing a target nucleotide subsequence or a set of target nucleotide subsequences, wherein if said first sample is probed with two or more recognition means, each recognition means recognizes a different target nucleotide subsequence or a different set of target nucleotide subsequences;

(c) generating one or more output signals from said first sample probed by said recognition means, each output signal comprising a representation of (i) the distance between occurrences of target nucleotide subsequences in said first nucleic acid, (ii) the identities of said target nucleotide subsequences in said first nucleic acid or the identities of said sets of target nucleotide subsequences among which are included the target nucleotide subsequences in said first nucleic acid; and (iii) a measure of the level/amount of the first nucleic acid in the first sample producing the output signal;

(d) performing steps (b) and (c) for said second sample; and (e) comparing the representation provided by said first sample with the representation provided by the second sample by generating a statistical score which states the probability that one or more output signals from said first sample indicates that one or more nucleotide sequences of said first sample are either present or absent in said second sample; and wherein said statistical score is generated by:

i) performing steps (a) through (d) on two or more independent samples of said first and said second sample;

ii) generating an average representation of said independent samples; and iii) generating a p-value from an f-test performed on said average representation.

13. The method of claim 12, wherein said p-value is between about 0.05 and about 0.10.

14. The method of claim 12, wherein said distance between occurrences of target nucleotide subsequences is pre-determined.

15. The method of claim 8, wherein said distance between occurrences of target nucleotide subsequences is pre-determined.

16. The method of claim 8, wherein said comparison is performed by generating (i) a statistical score which states the probability that one or more output signals from said first sample indicates that one or more nucleotide sequences of said first sample are either present or absent in said second sample; and (ii) a statistical score of a false-negative rate.

17. The method of claim 8, wherein said comparison is performed by generating (i) a statistical score which states the probability that one or more output signals from said first sample indicates that one or more nucleotide sequences of said first sample are either present or absent in said second sample; and (ii) a statistical score of a false-positive rate.

18. A method for identifying or classifying one or more nucleic acids in a first sample comprising a first population of first nucleic acids having different nucleotide sequences, said method comprising:

(a) probing said first sample with one or more recognition means, each recognition means recognizing a target nucleotide subsequence or a set of target nucleotide subsequences, wherein if said first sample is probed with two or more recognition means, each recognition means recognizes a different target nucleotide subsequence or a different set of target nucleotide subsequences, and wherein the probing comprises the steps of (i) contacting the first sample with the recognition means to provide an amplification mixture, and (ii) conducting an amplification process on said amplification mixture;

(b) generating one or more output signals from said first sample probed by said recognition means, each output signal comprising a representation of (i) the distance between occurrences of target nucleotide subsequences in said first nucleic acid, and (ii) the identities of said target nucleotide subsequences in said first nucleic acid or the identities of said sets of target nucleotide subsequences among which are included the target nucleotide subsequences in said first nucleic acid; and (c) comparing each representation provided by said first sample with a second population of second nucleic acids having different nucleotide sequences, wherein the different nucleotide sequences of said second population are known, by generating a statistical score which states the probability that one or more output signals from said first sample indicates that one or more nucleic acid sequences of said first sample are either present or absent in said second sample;

whereby said indication of presence or absence provides said identification or classification.

19. The method of claim 18, wherein the output signals from said first sample indicate that one or more nucleotide sequences of said first sample are present in said second sample.

20. The method of claim 18, wherein the output signals from said first sample indicate that one or more nucleotide sequences of said first sample are absent in said second sample.

21. A method for identifying or classifying one or more nucleic acids in a first sample comprising a first population of first nucleic acids having different nucleotide sequences, said method comprising:
   (a) probing said first sample with one or more recognition means, each recognition means recognizing a target nucleotide subsequence or a set of target nucleotide subsequences, wherein if said first sample is probed with two or more recognition means, each recognition means recognizes a different target nucleotide subsequence or a different set of target nucleotide subsequences, and wherein the probing comprises the steps of (i) contacting the first sample with the recognition means to provide an amplification mixture, and (ii) conducting an amplification process on said amplification mixture;
   (b) generating one or more output signals from said first sample probed by said recognition means, each output signal comprising a representation of (i) the distance between occurrences of target nucleotide subsequences in said first nucleic acid, and (ii) the identities of said target nucleotide subsequences in said first nucleic acid or the identities of said sets of target nucleotide subsequences among which are included the target nucleotide subsequences in said first nucleic acid;
   (c) performing steps (a) and (b) for a second population of second nucleic acids having different nucleotide sequences, wherein the different nucleotide sequences of said second population are not known;
   (d) comparing each representation provided by said first sample with said second sample, by generating a statistical score which states the probability that one or more output signals from said first sample indicates that one or more nucleotide sequences of said first sample are either present or absent in said second sample;
whereby said indication of presence or absence provides said identification or classification.

22. The method of claim 21, wherein the output signals from said first sample indicate that one or more nucleotide sequences of said first sample are present in said second sample.

23. The method of claim 21, wherein the output signals from said first sample indicate that one or more nucleotide sequences of said first sample are absent in said second sample.

24. A method for identifying, classifying, or quantifying one or more nucleic acids in a first sample comprising a first population of first nucleic acids having different nucleotide sequences, said method comprising:
   (a) probing said first sample with one or more recognition means, each recognition means recognizing a target nucleotide subsequence or a set of target nucleotide subsequences, wherein if said first sample is probed with two or more recognition means, each recognition means recognizes a different target nucleotide subsequence or a different set of target nucleotide subsequences, and wherein the probing comprises the steps of (i) contacting the first sample with the recognition means to provide an amplification mixture, and (ii) conducting an amplification process on said amplification mixture;
   (b) generating one or more output signals from said first sample probed by said recognition means, each output signal comprising a representation of (i) the distance between occurrences of target nucleotide subsequences in said first nucleic acid, (ii) the identities of said target nucleotide subsequences in said first nucleic acid or the identities of said sets of target nucleotide subsequences among which are included the target nucleotide subsequences in said first nucleic acid, and (iii) a measure of the level/amount of the first nucleic acid in the first sample producing the output signal; and
   (c) comparing each representation provided by said first sample with a second population of second nucleic acids having different nucleotide sequences, wherein the different nucleotide sequences of said second population are known, by generating a statistical score which states the probability that one or more output signals from said first sample indicates that one or more nucleotide sequences of said first sample are either present or absent in said second sample;
whereby said indication of presence or absence provides said identification, classification, or quantitation.

25. The method of claim 24, wherein the output signals from said first sample indicate that one or more nucleotide sequences of said first sample are present in said second sample.

26. The method of claim 24, wherein the output signals from said first sample indicate that one or more nucleotide sequences of said first sample are absent in said second sample.

27. A method for identifying, classifying, or quantifying one or more nucleic acids in a first sample comprising a first population of first nucleic acids having different nucleotide sequences, said method comprising:
   (a) probing said first sample with one or more recognition means, each recognition means recognizing a target nucleotide subsequence or a set of target nucleotide subsequences, wherein if said first sample is probed with two or more recognition means, each recognition means recognizes a different target nucleotide subsequence or a different set of target nucleotide subsequences, and wherein the probing comprises the steps of (i) contacting the first sample with the recognition means to provide an amplification mixture, and (ii) conducting an amplification process on said amplification mixture;
   (b) generating one or more output signals from said first sample probed by said recognition means, each output signal comprising a representation of (i) the distance between occurrences of target nucleotide subsequences in said first nucleic acid, (ii) the identities of said target nucleotide subsequences in said first nucleic acid or the identities of said sets of target nucleotide subsequences among which are included the target nucleotide subsequences in said first nucleic acid, and (iii) a measure of the level/amount of the first nucleic acid in the first sample producing the output signal;
   (c) performing steps (a) and (b) for a second population of second nucleic acids having different nucleotide sequences, wherein the different nucleotide sequences of said second population are not known; and
   (d) comparing each representation provided by said first sample with said second sample, by generating a statistical score which states the probability that one or more output signals from said first sample indicates that one or more nucleotide sequences of said first sample are either present or absent in said second sample; whereby said indication of presence or absence provides said identification, classification or quantitation.

28. The method of claim 27, wherein the output signals from said first sample indicate that one or more nucleotide sequences of said first sample are present in said second sample.

29. The method of claim 27, wherein the output signals from said first sample indicate that one or more nucleotide sequences of said first sample are absent in said second sample.

30. The method of any of claims 18, 21, 24 or 27, wherein said statistical score is generated according to Bayes Rule of conditional probability, wherein said statistical score is related to the conditional probability that one or more second nucleic acids from said second population occurs in said first population when one or more representations of a first set of said first nucleic acids are present in said one or more output signals and no representation of a second set of first nucleic acids is present in said one or more output signals.

31. The method of any of claims 18, 21, 24 or 27, wherein said indication that one or more nucleotide sequences of said first sample is present in said second sample is established when the conditional probability that an output signal is detected when no second nucleic acid is present in said second population is less than a predetermined limit.

32. The method of claim 31, wherein said predetermined limit is less than about 0.1.

33. The method of claim 31, wherein said predetermined limit is less than about 0.01.

34. The method of claim 31, wherein said predetermined limit is less than about 0.001.

35. The method described in any of claims 18, 21, 24 or 27, wherein the recognition means comprises one or more restriction endonucleases and the probing comprises contacting said first sample with said recognition means.

36. The method described in any of claims 18, 21, 24 or 27, wherein the recognition means comprises one or more oligonucleotides of defined sequence.

* * * * *